(12) United States Patent
Sawafta

(10) Patent No.: US 6,898,549 B1
(45) Date of Patent: May 24, 2005

(54) AUTOMATED SYSTEMS FOR WEIGHING AND/OR LIQUID DELIVERY

(75) Inventor: Reyad Sawafta, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 18 days.

(21) Appl. No.: 10/332,114

(22) PCT Filed: Jul. 6, 2001

(86) PCT No.: PCT/US01/41301

§ 371 (c)(1),
(2), (4) Date: Jan. 6, 2003

(87) PCT Pub. No.: WO02/04900

PCT Pub. Date: Jan. 17, 2002

Related U.S. Application Data

(63) Continuation-in-part of application No. 09/611,393, filed on Jul. 7, 2000, now Pat. No. 6,539,334.

(51) Int. Cl.[7] .......................... G01G 17/06; G01N 35/00
(52) U.S. Cl. .................... 702/175; 702/173; 177/25.11; 141/165
(58) Field of Search ................................ 702/175, 173; 177/25.11; 141/165

(56) References Cited

U.S. PATENT DOCUMENTS

| | | | |
|---|---|---|---|
| 4,913,198 A | | 4/1990 | Hayahara et al. |
| 4,976,377 A | * | 12/1990 | Higuchi et al. ................ 222/55 |
| 5,660,792 A | | 8/1997 | Koike |
| 5,769,775 A | | 6/1998 | Quinlan et al. |
| 5,835,982 A | * | 11/1998 | Lanaro et al. ............... 177/145 |
| 5,985,214 A | | 11/1999 | Stylli et al. |
| 5,993,744 A | * | 11/1999 | Rao et al. .................... 422/103 |
| 6,387,330 B1 | * | 5/2002 | Bova et al. .................. 422/100 |
| 6,455,002 B1 | * | 9/2002 | Jokes et al. .................... 422/63 |
| 6,539,334 B1 | | 3/2003 | Sawafta |

FOREIGN PATENT DOCUMENTS

| | | | |
|---|---|---|---|
| DE | 197 22 091 A1 | 12/1998 | |
| DE | 19722091 A1 | * 12/1998 | ........... G01G/11/00 |
| EP | 1 003 020 A1 | 5/2000 | |
| EP | 0 769 686 B1 | 12/2001 | |
| WO | WO98/01760 | 1/1998 | |
| WO | WO99/15905 | 4/1999 | |

OTHER PUBLICATIONS

Brochure—"Balance Automator™, Round–the–Clock Weighing Station," LIT–BO2–1098, Bohdan Automation, Inc. (1998).
Brochure—"Automation Your Way Today, Automated Weighing/Labeling Workstation," dlit01 199, Bohdan Automation, inc. (date unknown).

(Continued)

*Primary Examiner*—Bryan Bui
*Assistant Examiner*—Anthony T. Dougherty
(74) *Attorney, Agent, or Firm*—Kilpatrick Stockton LLP

(57) ABSTRACT

An automated weighing station is provided which is advantageous for automatically weighing samples generally disposed in containers in an array of racks. The weighing station comprises a sample handling assembly which is operably connected to a balance, allowing a moveable sample carrier to bring samples into position beneath the balance and sample handling assembly, thereby minimizing the movement of individual samples in order to accomplish weighing. A weighing system that provides flexibility and convenience in generating and transforming a variety of data sets associated with measurements accomplished using the weighing apparatus is also provided. Also disclosed is an automated liquid dispensing system for dispensing liquid into sample containers. The liquid dispensing system may operate independently or in conjunction with the weighing system in a synchronized fashion.

42 Claims, 16 Drawing Sheets

OTHER PUBLICATIONS

Brochure—"Automated Weighing, Automated Labeling, Synthesis Support, High Throughput Synthesis, Process Development," LIT–GEN1–100, Bohdan Automation, inc. (date unknown).

Brochure—J–KEM Scientific Custom Robotics & Accessories; www.jkem.com.

International Search Report mailed Nov. 13, 2001 corresponding to PCT/US 01/41301.

* cited by examiner

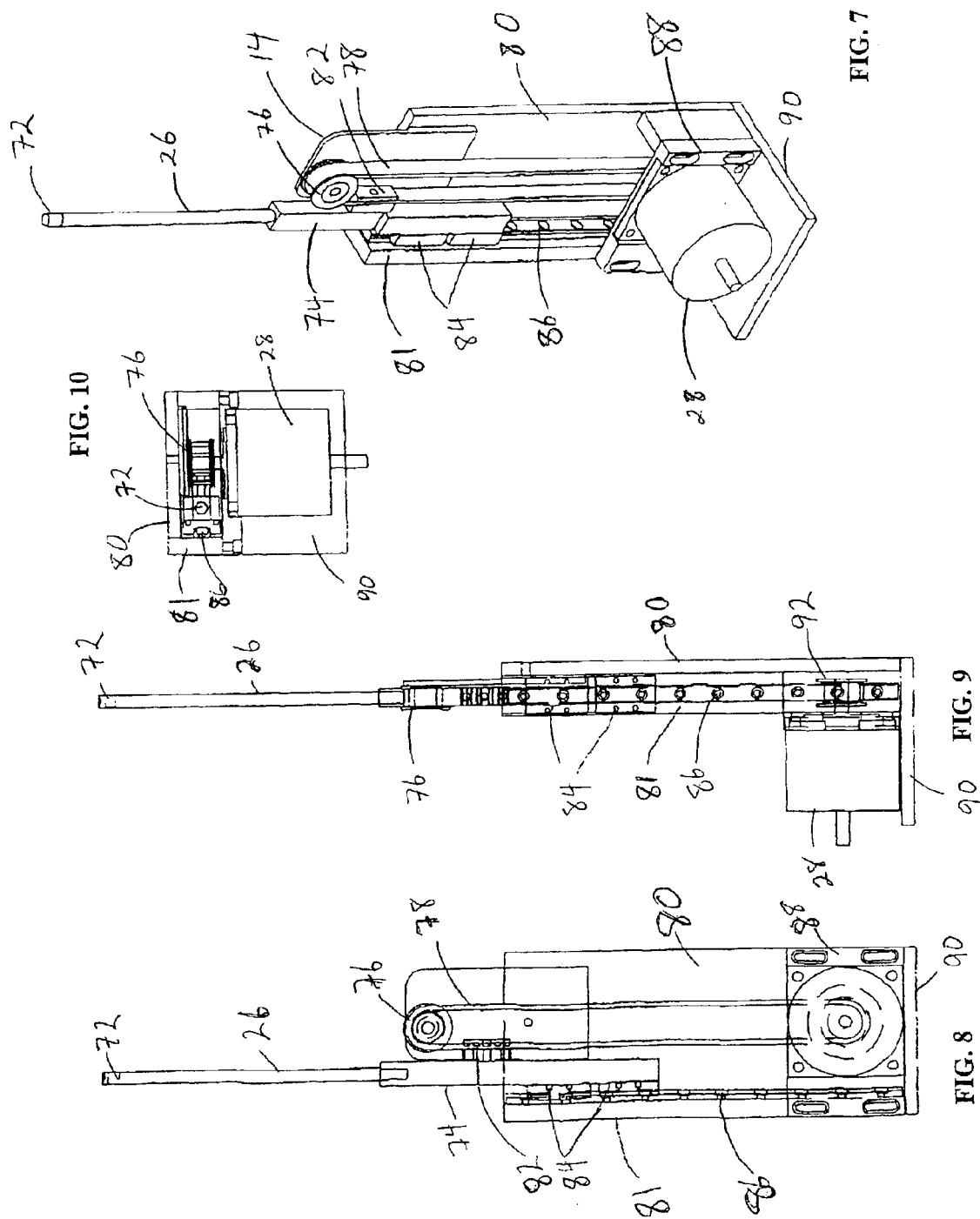

Figure 17

| Select | Rack | Barcode Number | Get Tare | Get Gross | Pump w/ Weight | Pump w/o Weight (uL) | Use Molarity | Concentration |
|---|---|---|---|---|---|---|---|---|
| ☑ | 01 | 71-6 | ☐ | ☑ | ☑ | ☐ | ☐ | 5.0 mg/ml |
| ☑ | 02 | 55-207 | ☐ | ☐ | ☐ | ☑ 3.0 | ☐ | mg/ml |
| ☑ | 03 | 71-5 | ☐ | ☑ | ☑ | ☐ | ☐ | 6.4 mg/ml |
| ☑ | 04 | 55-205 | ☐ | ☐ | ☐ | ☑ 4.0 | ☐ | mg/ml |
| ☑ | 05 | 71-11 | ☐ | ☑ | ☑ | ☐ | ☐ | 2.8 mg/ml |
| ☑ | 06 | 55-206 | ☐ | ☐ | ☐ | ☑ 5.0 | ☐ | mg/ml |
| ☑ | 07 | 71-12 | ☐ | ☑ | ☑ | ☐ | ☐ | 7.0 mg/ml |
| ☑ | 08 | 71-8 | ☐ | ☐ | ☐ | ☑ 2.0 | ☐ | mg/ml |
| ☑ | 09 | 71-9 | ☐ | ☑ | ☑ | ☐ | ☐ | 4.5 mg/ml |
| ☑ | 10 | 71-10 | ☐ | ☐ | ☐ | ☑ 1.5 | ☐ | mg/ml |
| ☑ | 11 | 55-208 | ☐ | ☑ | ☑ | ☐ | ☐ | 4.0 mg/ml |
| ☑ | 12 | 71-7 | ☐ | ☐ | ☐ | ☑ | ☐ | mg/ml |

AUTOMATED SYSTEMS FOR WEIGHING AND/OR LIQUID DELIVERY

STATEMENT OF RELATED APPLICATIONS

The present application is a continuation in part application of U.S. patent application Ser. No. 09/611,393, filed Jul. 7, 2000, now U.S. Pat. No. 6,539,334 entitled "Automated Weighing Station" the disclosure of which is hereby incorporated herein by reference.

FIELD OF THE INVENTION

The present invention relates to apparatus for weighing and/or dispensing liquid. Embodiments of the present invention are advantageous for automatically weighing and/or dispensing liquid into small samples generally disposed in containers in an array of racks. The invention also relates to weighing and liquid dispensing systems that provide flexibility and convenience in generating and transforming a variety of data sets associated with measurements accomplished using the weighing and/or liquid dispensing apparatus.

BACKGROUND

Recently, the proliferation of combinatorial libraries in high throughput synthesis and screening (HTS) programs have led to an ever increasing emphasis on automation. The ability to prepare and test a large number of compounds quickly can provide a competitive advantage. Thus, automated preparation and evaluation has become a key process in lead discovery.

The recent explosion in the number of compounds available for screening, and the expected increase in compounds with the development of automated chemical synthesis, has meant that a large number of pharmaceutical and other chemical companies are in need of automated weighing of such compounds. However, several difficulties have been encountered in attempts to provide a fast, efficient, and cost-effective solution to the problem of automatically weighing large numbers of small samples.

Proposed solutions which simply implement robotic methods to remove and replace samples from racks to facilitate weighing present significant problems. Robotic fingers have difficulty in grasping individual samples for removal from among an array of closely placed samples in a rack. Certain devices function only with flat bottom containers, which are more difficult to return to the rack after weighing. Misplacement during return may result in spilling of the sample contents, or breakage of one or more samples (possible leading to contamination of one or more samples).

A major difficulty unsolved by current devices is the lack of speed when weighing a large number of samples. Current devices generally employ a robotic sample transfer assembly, which retrieves a sample from an array, transfers the sample to a separate balance, and then returns the sample container to a particular position in a holder, such as a test tube rack. Although some such systems may have the ability to identify the particular sample, and associate the sample with the measurement taken to enable later data recordation and processing, systems currently employed require a large amount of inefficient and time-consuming movement. The sample must be plucked from an array, moved to the balance, isolated from the surrounding environment by closing a door of a chamber surrounding the balance, retrieved from the balance after opening the door of the chamber, moved back into position relative to the array, and returned to the sample's original position. Thus, having the balance a considerable distance from the actual sample position within an array leads to a great deal lost time in moving each sample to and from the balance.

Current devices also handle a relatively limited number of samples during each run. It would be advantageous to provide an automated system which is capable of handling a larger number of samples than those devices currently available.

Accordingly, it is one object of the present invention to provide an automated weighing system which handles a larger number of samples per run than currently available devices. It is also an object of the invention to accomplish weighing of a large number of samples in less time, and with increased accuracy, handling efficiency and reliability. Additionally, another object of the invention is to provide a weighing system allowing increased control of an automated weighing apparatus, and increased versatility in data collection, storage and transformation.

An additional object of the present invention is to provide an automated system for dispensing liquid which handles a larger number of samples per run than currently available devices. It is also an object of the invention to accomplish filling of a large number of sample containers in less time, and with increased handling efficiency and reliability.

SUMMARY OF THE INVENTION

The present invention provides a solution to many current problems associated with automated weighing of large numbers of samples. One advantage is that the overall movement of individual samples to accomplish the weight measurement is minimized. This reduces the time required, and reduces the likelihood of malfunctions such as breakage of sample containers and/or contamination of samples.

Accordingly, in one aspect the invention relates to an automated weighing station comprising a support frame, a balance secured to the support frame, a sample handling assembly, that may be isolated from the surrounding environment, operably connected to the balance and secured to the balance, a moveable carrier for moving samples into position beneath the sample handling assembly, a lift assembly positioned beneath the moveable carrier and the sample handling assembly for lifting samples into position to be accessed by the sample handling assembly, and a control system for controlling the sample handling assembly, the lift assembly, and the moveable carrier in a coordinated manner, and for storing weight measurements of individual samples. The control system also provides a user interface.

In another aspect, the invention relates to a method of weighing multiple individual samples comprising moving an ordered array of sample containers beneath a stationary sample handling assembly, elevating at least one sample container, reversibly securing the at least one sample container to a gripper assembly of the stationary sample handling assembly, and returning the at least one sample container to the ordered array after a weight measurement is taken, wherein the gripper assembly is connected to a balance, and is disengaged from other components of the sample handling assembly while the weight measurement is taken.

In yet another aspect, the invention relates to a weighing system for automated weighing of samples comprising a support frame; a balance secured to the support frame; a sample handling assembly operatively connected to the balance and secured to the balance; a moveable carrier for moving samples into position beneath the sample handling assembly; a lift assembly positioned beneath the moveable carrier and the sample handling assembly for lifting samples into position to be accessed by the sample handling assembly; and a data handling system for storing and processing of weight measurements of the samples.

The invention provides many of the benefits described herein by virtue of the close association of the sample handling assembly, including the gripper or lift assemblies, with the balance where the weight measurement is taken. The benefits provided by the invention are described in greater detail below.

The present invention also provides a solution to many current problems associated with automated delivery of liquid to large numbers of samples or sample containers. One advantage is that the overall movement of individual samples to accomplish the liquid dispensing is minimized. This reduces the time required, and reduces the likelihood of malfunctions such as breakage of sample containers and/or contamination of samples.

Accordingly, in one aspect the invention relates to an automated liquid delivery system comprising a support frame, a liquid delivery apparatus comprising a liquid reservoir in communication with a pump and a liquid dispensing nozzle, a sample handling assembly operably connected to the liquid dispensing nozzle, a moveable carrier for moving samples into position beneath the sample handling assembly, and a control system for controlling the sample handling assembly, the moveable carrier and the dispensing of liquid in a coordinated manner. The control system also provides a user interface. The liquid delivery system may be utilized to add one or more liquids, or combinations of liquids, to fresh sample containers (e.g. test tubes) in specified increments. The liquid delivery system may also be advantageously utilized to deliver liquid to sample containers containing samples for dilution or other purposes, such as to modify concentrations of liquids already part of the sample.

The liquid delivery system may include a probe for measuring properties of liquids in a sample or sample container. For example, in embodiments of the present invention, a probe could be utilized to measure the pH or other properties of a sample solution in a test tube. In embodiments of the present invention the liquid delivery system may be utilized to deliver water, aqueous solutions, solvents, solvent solutions and/or other liquids.

In another aspect, the invention relates to a method of dispensing liquid into multiple individual samples comprising moving an ordered array of sample containers beneath a liquid dispensing apparatus nozzle and dispensing a liquid.

In a further aspect, the invention relates to weighing systems and methods as set forth above further comprising a liquid delivery system. In a system of the present invention, the liquid delivery system may be configured to deliver liquid simultaneously, or immediately before or after, weighing. Alternatively, the liquid delivery system may be configured to deliver liquid independently from the weighing operation, or to deliver liquid to one sample while another sample is being weighed, etc.

In another aspect, the invention relates to data acquisition and control system for weighing systems, liquid dispensing systems, such as the weighing systems and liquid dispensing systems described above, including weighing systems comprising liquid delivery systems. An embodiment of a control system may be implemented utilizing computer software and related hardware. The control and data acquisition system may be advantageously utilized to provide uniform or individual liquid delivery for samples based on either an equal concentration or an equal molarity for each sample. The control and data acquisition system may also be utilized to control component parts of the weighing system, for example to control gripping and weighing of samples, movement of sample trays, dispensing of liquid and the like.

In embodiments of the present invention, data generated by the automated weighing of samples is maintained in electronic form and fed electronically into a computer hardware and software implemented data acquisition system. The data may comprise information relating to the characteristics of particular samples, for example, weight, molarity, pH and/or the like. Alternatively, or in addition, the data may comprise information relating to the weighing system as a whole, or component parts of the weighing system, for example number of sample weighed, current sample and rack, weighing time per sample and the like. The data acquisition system may be implemented utilizing software that may be easily integrated to other databases including, but not limited to, for example Oracle or Microsoft Access.

Embodiments of weighing systems according to the present invention may further comprise bar code scanning means for reading bar codes on samples or sample racks. The data generated may be communicated to the data acquisition system and incorporated into a database.

Further, embodiments of weighing systems of the present invention may include monitoring or safety means for monitoring the automated actions of the system components to ensure the components are properly positioned before movement to minimize component breakage. The monitoring means may comprise sensors, laser scanners and/or similar hardware in communication with a control system that will suspend operation of the weighing system component or components if a situation that could potentially damage the weighing system or a component thereof is sensed.

The systems of the present invention provide many advantages over prior systems for weighing multiple samples or for dispensing liquid.

Weighing systems of the present invention advantageously provide a weighing process that is accurate and reproducible with an accuracy of weighing up to 0.1 mg or greater.

Weighing systems of the present invention may be utilized for weighing, liquid delivery or for combination of both. One can load racks of samples and perform either weighing the samples alone, or delivering solvents to these samples alone or weighing the samples and deliver liquid to them. This can be done in any combination for each individual rack.

Features of the systems of the present invention enhance productivity and quality in industry, many research, analytical and QC laboratory applications. In pharmaceutical applications, systems of the present invention may be advantageously utilized in systems for compound yield determination; compound management; and/or stability/shelf-life determinations. In chemical applications, systems of the present invention may be advantageously utilized in systems for weight determination of powders and solids; stability/shelf-life determination and/or HPLC or GC preparation. In food and cosmetic applications, systems of the present invention may be advantageously utilized in systems for sample preparation.

Embodiments of the present invention may provide one or more of the following advantages:

Automated, hands-free weighing, thereby providing repeatable accuracy and freeing laboratory staff to perform other duties;

Automated, hands-free liquid delivery, thereby ensuring accuracy and freeing laboratory staff to perform other duties;

Error free documentation;

Rapid sample rates in terms of samples weighed/filled per hour;

Configurable for use with vials, test tubes, mini-tubes and/or other sample carriers; and Bar code scanning of samples and/or sample trays.

Embodiments of the weighing systems of the present invention may be configured to hold hundreds or thousands of samples and weigh hundreds of samples, or more, per hour, on a bottom-loading high accuracy analytical balance such as a four, five or six place analytical balance. An apparatus of the present invention can be optionally configured with multiple formats such as, but not limited to, with 48 or 96 test tube rack configurations. Embodiments of the weighing systems of the present invention may also be configured to hold multiple racks of vials, test tubes, and/or mini-tubes that can be tarred and reweighed as required. Embodiments of the present invention provide high throughput reliable weighing and liquid delivery that is accurate and fast.

An additional advantage of an embodiment of the present invention that comprises a weighing system and a liquid dispensing system is that the weighing system and the liquid dispensing system may operate in a synchronized fashion to reduce the amount of time for both functions to be performed on each sample. For example, the liquid dispensing system may fill sets of samples while other sets of samples are being weighed. As a result, the overall time to both weigh and fill samples with liquid in not substantially increased over the time it would take to either weigh or fill the samples with liquid.

A further advantage of the present invention is that embodiments of the present invention may comprise a data acquisition and control system that may be advantageously utilized to control the weighing of samples and/or the dispensing of liquid and may further collect and store data relating to samples in a format that can be accessed and utilized by other databases.

BRIEF DESCRIPTION OF THE DRAWINGS

FIG. 7 is a perspective view of an embodiment of the sample lift assembly (viewed as from the upper right rear to the lower, left front of the view of FIG. 2).

FIG. 8 is an elevational view of an embodiment of the sample lift assembly (viewed as from the right of FIG. 2).

FIG. 9 is an elevational view of an embodiment of the sample lift assembly (viewed as from the right of FIG. 8).

FIG. 10 is a top elevational view of an embodiment of the sample lift assembly.

FIGS. 17–20 depict screenshots from an embodiment of a graphical user display in a data acquisition and control system of the present invention.

In the Figures, like reference characters indicate corresponding parts.

DETAILED DESCRIPTION OF THE INVENTION

Figure 1:
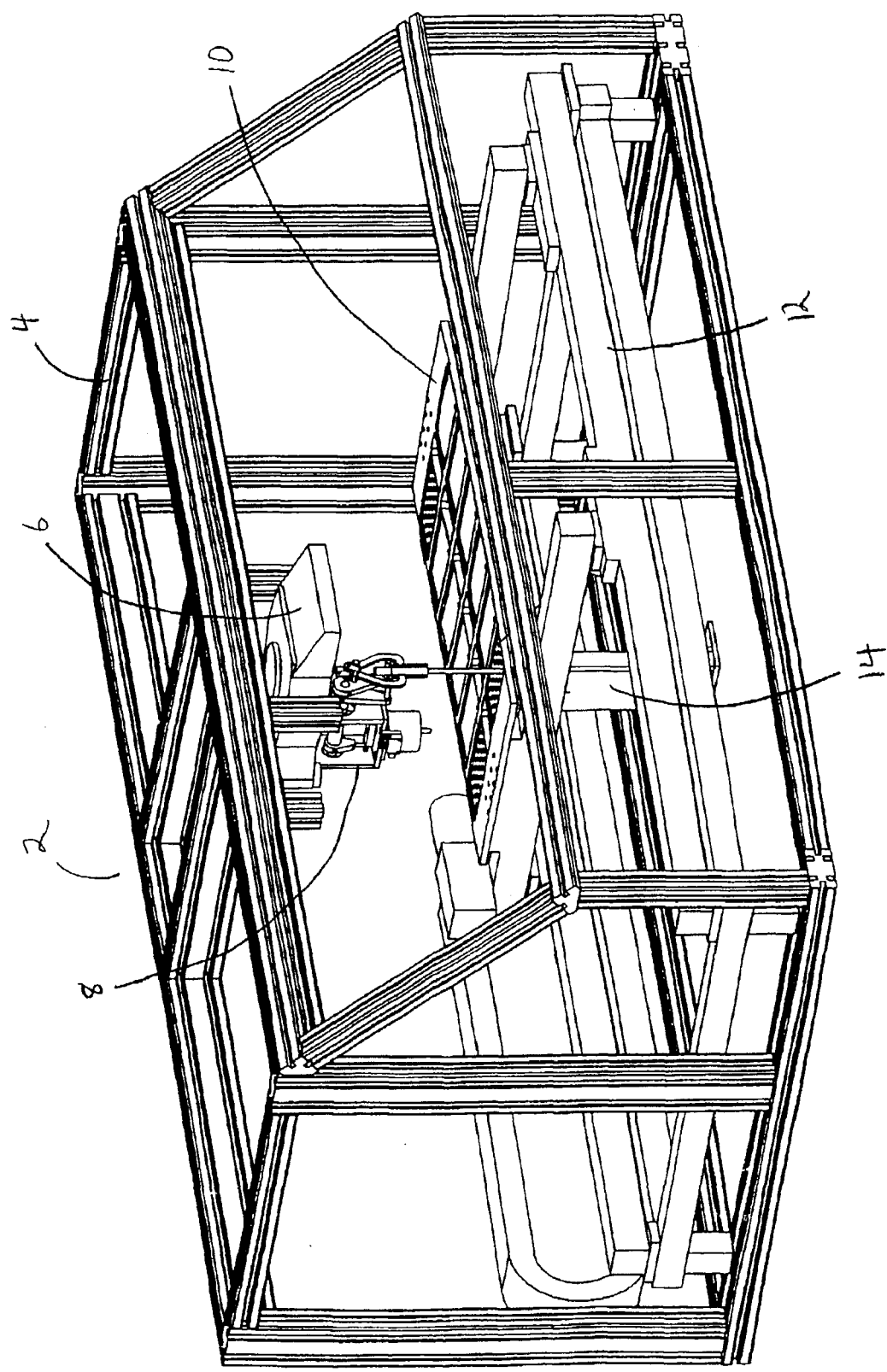
FIG. 1 is a front perspective view of one embodiment of the apparatus of the invention.

The present invention provides solutions to many problems associated with automated weighing of multiple samples. In particular, the present invention allows large numbers of samples to be weighed rapidly. The invention also allows samples to be weighed with decreased opportunity for breakage and/or sample contamination.

Accordingly, in one aspect the invention relates to an automated weighing station comprising a support frame, a balance secured to the support frame, a sample handling assembly operably connected to the balance and secured to the balance, a moveable carrier for moving samples into position beneath the sample handling assembly, a lift assembly positioned beneath the moveable carrier and the sample handling assembly for lifting samples into position to be accessed by the sample handling assembly, and a control system for controlling the sample handling assembly, the lift assembly, and the moveable carrier in a coordinated manner, and for storing weight measurements of individual samples. The moveable carrier is coordinated with the operation of the lift assembly and the sample handling assembly via multiple positioning sensors which output to the control system, allowing rapid and safe handling of the samples, as well as providing data allowing each sample to be individually identified with its corresponding weight measurement when the data is stored or transferred in electronic form.

In a preferred embodiment, the sample handling assembly further comprises a gripper assembly comprising arms, one end of each arm being pivotably connected along a common pivot axis, and the opposite end of each arm comprising a gripper finger adapted to directly contact a sample container; a spring tensioner urging the arms toward one another; and a powered mechanical drive component in communication with the gripper assembly. More preferably, the mechanical drive component operates intermittently to spread the gripper arms against the force of the spring tensioner, thereby increasing the distance between the gripper fingers of the respective gripper arms such that a sample may be received therein, to be gripped by the fingers when the mechanical drive component releases the arms to return to a closed position as urged by the spring tensioner. The gripper assembly is designed to be small and light enough such that the net weight of individual samples is accurately weighed and recorded while the gripper assembly is operable connected to a component of the balance to actuate the weighing mechanism of the balance. When the actual weight measurement is accomplished, the mechanical drive component is dissociated from the gripper assembly, such that it does not interfere with an accurate measurement.

In another preferred embodiment, the moveable carrier comprises a sample rack carrier and a carrier support unit. More preferably, position sensors are provided which are adapted to communicate the position of the sample rack carrier in relation to the gripper assembly to the control system such that weight measurements of individual samples are stored electronically, and are associated with an individual sample by at least one identifying characteristic. Also more preferably, the sample racks are characterized by an asymmetric shape which requires that the sample racks be placed in the sample rack carrier in only one possible orientation relative to the moveable carrier. Also more preferably, a scanner is provided for determining the identity of sample racks within an array of racks held by the sample rack carrier. Also more preferably, the sample rack carrier comprises openings such that the scanner may determine the identity of sample racks disposed within the interior of the array of racks. More preferably, the sample racks are identified by the scanner utilizing a bar coding system. The sample rack carrier may be adapted to hold at least one rack which is adapted to hold a plurality of sample containers. More preferably, the sample rack carrier is adapted to allow access by the lift assembly to at least one sample container from beneath the sample rack carrier. This feature of the present invention provides significant benefits by allowing the overall movement of individual samples to be minimized, and controlled, because samples are moved in a short, substantially vertical path from the sample rack to the gripper assembly.

In a preferred embodiment, the carrier support unit further comprises at least one powered mechanical drive component adapted to provide controlled forward and rearward, left and right movement of the sample rack carrier. More preferably, the at least one powered mechanical drive component comprises a first electric motor controlling forward and rearward movement, and a second electric motor controlling left and right movement of the sample rack carrier. Additionally, position sensors outputting to the control system provide data allowing the individual identity of sample to be associated with their respective weight measurements as stored data.

In another preferred embodiment, the lift assembly comprises a housing; a powered mechanical drive component connected to the housing; and a lift shaft operably connected to the powered mechanical drive component, wherein the powered mechanical drive component provides controlled upward and downward movement of the lift shaft. More preferably, the lift shaft further comprises a tip which is adapted to receive the bottom portion of a sample container. More preferably, the tip is adapted to receive a bottom portion of a sample container, the shape of which is selected from the group consisting of rounded, conical, flat-ended cubical, and flat-ended circular. Most preferably, the powered mechanical drive component comprises an electric motor having a pulley engaged to a belt member, the distal portion of which engages a second pulley, and wherein the belt member is attached to a lift shaft mount to provide upward and downward motion of the lift shaft which is connected to the lift shaft mount. Position sensors allow coordination of the lift shaft movement with sample position relative to the moveable carrier and the sample handling assembly. These position sensors output to the control system to facilitate rapid but safe and efficient sample handling in conjunction with the operation of the sample handing assembly.

In another preferred embodiment, the automated weighing station further comprises a housing adapted to isolate a gripper assembly of the sample handling assembly. More preferably, the housing comprises a first sensor associated with an aperture for receiving a sample through a bottom plate of the housing, and a second sensor positioned adjacent to the gripper assembly, the first and second sensors allowing determination of a lowered position and a lifted position, respectively, of the sample. Most preferably, the housing further comprises at least one aperture for the introduction of gases for atmospheric control within the housing. The sensors output to the control system, allowing control of other moving components of the station, in conjunction with sample movement into, and out of, the housing.

In another aspect, the invention relates to a method of weighing multiple individual samples comprising moving an ordered array of sample containers beneath a stationary sample handling assembly, elevating at least one sample container, reversibly securing the at least one sample container to a gripper assembly of the stationary sample handling assembly, and returning the at least one sample container to the ordered array after a weight measurement is taken, wherein the gripper assembly is connected to a balance and is disengaged from other components of the sample handling assembly while the weight measurement is taken.

In a preferred embodiment, the weight of a sample within the individual sample container is between about 0.01 mg and about 500 g. More preferably, the weight of a sample within the individual sample container is between about 0.1 mg and about 50 g. Most preferably, the weight of a sample within the individual sample container is between about 1 mg and about 5 g. In a preferred embodiment, the weight of a sample within the individual sample container is between about 1 mg and about 100 mg. More preferably, the weight of a sample within the individual sample container is between about 2 mg and about 50 mg. Most preferably, the weight of a sample within the individual sample container is between about 5 mg and about 25 mg.

The design of the gripper assembly and its operation by the mechanical drive component of the sample handling assembly allows accurate and precise measurements of net sample weight.

In yet another aspect, the invention relates to a weighing system for automated weighing of samples comprising a support frame; a balance secured to the support frame; a sample handling assembly operatively connected to the balance and secured to the balance; a moveable carrier for moving samples into position beneath the sample handling assembly; a lift assembly positioned beneath the moveable carrier and the sample handling assembly for lifting samples into position to be accessed by the sample handling assembly; and a data handling system for storing and processing of weight measurements of the samples.

In a preferred embodiment, the data handling system comprises a balance; computer software; and computer hardware; wherein the data handling system is adapted to communicate weight measurements to computer software and hardware. More preferably, the data handling system further comprises one or more data collectors positioned and adapted to transmit information to a computer control unit, thereby allowing coordinated movement of samples via the sample handing assembly, the moveable carrier, and the lift assembly, wherein the information is coordinated by the computer control unit with the storage of weight measurement transmitted by the balance for individual samples. Most preferably, the data handling system further comprises a scanner for detection of the position and identity of sample racks on the moveable carrier; at least one position sensor associated with the moveable carrier; and at least one sample position sensor associated with the sample handling assembly.

In another preferred embodiment, the computer hardware of the data handling system comprises one or more of the following: a display; data entry apparatus; a processor, an interface to the weighing apparatus; a printer or other output apparatus; electronic interfaces among the component parts; and memory.

In another preferred embodiment, the computer software of the data handling system comprises an operating system; a database program; a report generating program; a data-receiving program for receiving data from the weighing apparatus; and a control program for controlling the weighing apparatus. More preferably, the report generating program is adapted to provide data comprising individual sample identification related to one or more of sample rack identity, sample position, tare weight of a sample container, gross weight of sample and sample container, and net weight of sample. More preferably, the data is originally stored in a format selected from the group consisting of ASCII text binary, and ODBC (object database connectivity format). Most preferably, the data is originally stored in ASCII text format. Other formats may also be employed for data storage and transfer in particular situations.

In another aspect the present invention relates to an automated liquid dispensing apparatus comprising a support frame, a liquid dispenser secured to the support frame, a sample handling assembly operably connected to the liquid dispenser, a moveable carrier for moving sample or sample containers into position beneath the sample handling assembly to permit filling of sample containers and a control system for controlling the sample handling assembly, the liquid dispenser, and the moveable carrier in a coordinated manner. The moveable carrier is coordinated with the operation of the liquid dispenser and the sample handling assembly via multiple positioning sensors which output to the control system, allowing rapid and safe handling of the samples, as well as providing data allowing each sample to be individually identified with its corresponding liquid measurement when the data is stored or transferred in electronic form.

A liquid dispenser for use in the present invention comprises a dispensing portion, comprising a nozzle or end of a tube or the like. The liquid dispenser further comprises a tube or similar apparatus connecting the dispensing portion and a source of liquid. The source of liquid may comprise a reservoir, or may comprise a connection to a source of fluid. In an embodiment of the present invention, the source of liquid comprises a standard laboratory reagent bottle and the liquid dispenser comprises a connection that replaces the cap of the reagent bottle.

The liquid dispenser will generally comprise a pump for moving liquid from the reservoir or source of liquid to the dispensing portion. The pump may be mounted on the frame of the apparatus, or in another location between the dispensing portion and the source of liquid.

Other aspects of the automated liquid dispensing apparatus of the present invention may be the same as similar aspects of the automated weighing station of the present invention wherein the liquid dispenser is substituted for the weighing apparatus.

In another aspect, the present invention provides a single apparatus that may be utilized for both the automated weighing of samples and for the automated dispensing of liquid. Embodiments of the this aspect of the present invention position the dispensing portion of the liquid dispenser in close proximity to the weighing apparatus to allow for the weighing of a sample and/or dispensing of liquid into the sample.

In a further aspect, the invention relates to a method of dispensing liquid into multiple individual samples comprising moving an ordered array of sample containers beneath a stationary sample handling assembly, positioning a liquid dispenser above at least one sample container; and dispensing liquid into the sample container.

As will be recognized by those of ordinary skill in the art, and as described above, embodiments of an automated liquid dispensing apparatus of the present invention may comprise a data handling system, or a data acquisition and control system similar to the ones described above with reference to an automated weighing station of the present invention. Further aspects of an embodiment of a data acquisition and control system are described below.

Referring now to the Figures, in particular to FIG. 1, a front perspective view of one embodiment of the automated weighing station 2 of the invention is shown. Enclosure and support frame 4 is shown supporting balance 6 and sample handling assembly 8. Also shown is sample lift assembly 14, sample rack carrier 10, and carrier support unit 12.

Frame 4 also provides support for materials which may be used in conjunction with frame 4 to enclose the automated weighing station 2. Frame 4 may be constructed so as to allow access via a front, lift-type door in a conventional fashion, and/or via side access door openings, such that samples may be easily accessed before, during, or at the conclusion of an automated weighing run.

Sample lift assembly 14 functions to raise an individual sample to facilitate access to the sample by the sample handling assembly 8. Accordingly, sample racks in sample rack carrier 10 have apertures beneath each individual sample compartment to allow access from below the sample. Carrier support unit 12 stably supports sample rack carrier 10, and transports carrier 10 laterally to allow each individual sample to be brought into handling positions beneath sample handling assembly 8.

Figure 2:
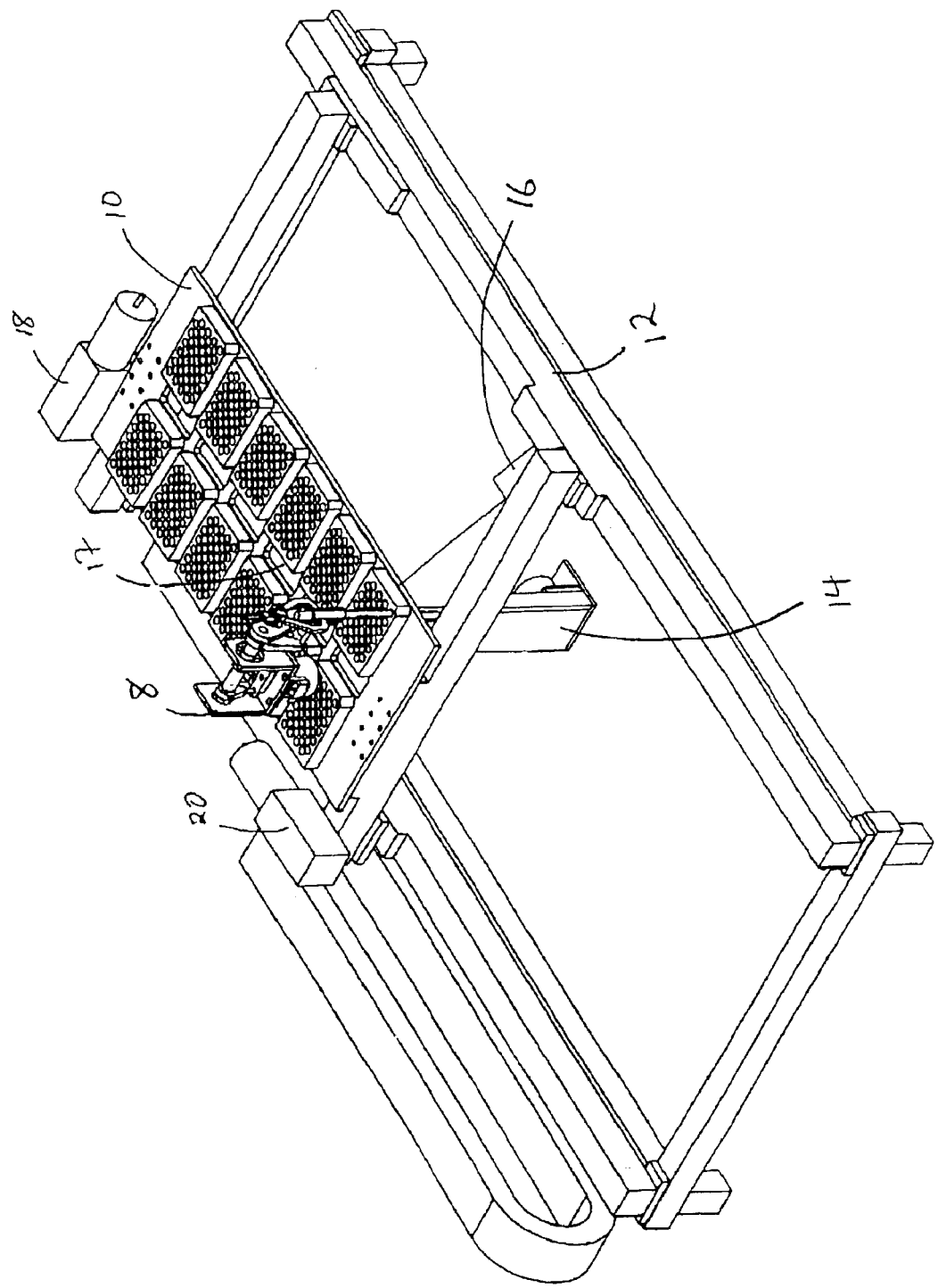
FIG. 2 is a cut-away, top perspective view of an embodiment of the apparatus of the invention (balance and upper frame portion not shown).
Figure 3:
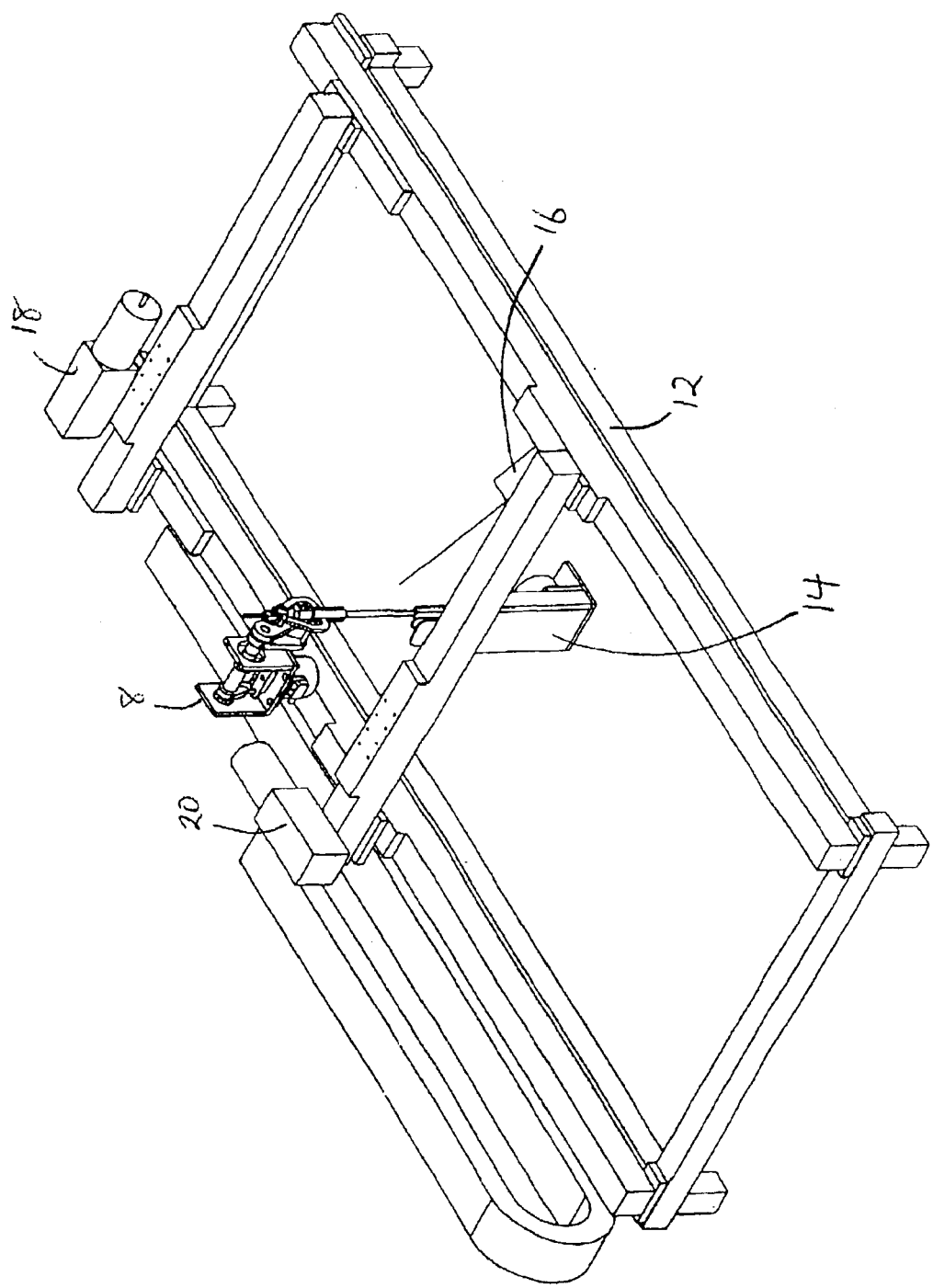
FIG. 3 is a cut-away, top perspective view of the apparatus of the invention as in FIG. 2 (sample racks and carrier not shown).

FIG. 2 shows an embodiment of the apparatus of the invention, without showing frame 4 or balance 6 as shown in FIG. 1. Motors 18 and 20 provide power for left-right, front-back movement of sample rack carrier 10 on carrier support unit 12. Scanner 16 reads identifying information on the end of each sample rack, e.g. a bar code. In FIG. 2, scanner 16 is shown reading the front row of racks in carrier 10. When the rear row of racks is being analyzed, scanner 16 reads the identifying information through apertures 17 in carrier 10. Because of asymmetry in rack design, samples positioned within each rack are necessarily identified by rack identification. FIG. 3 is very similar to FIG. 2, except the sample racks and sample rack carrier 10 are not shown. Sample lift assembly is shown mounted on carrier support unit 12, and interacting with a sample container to facilitate reception of a sample by sample handling assembly 8.

Figure 4:
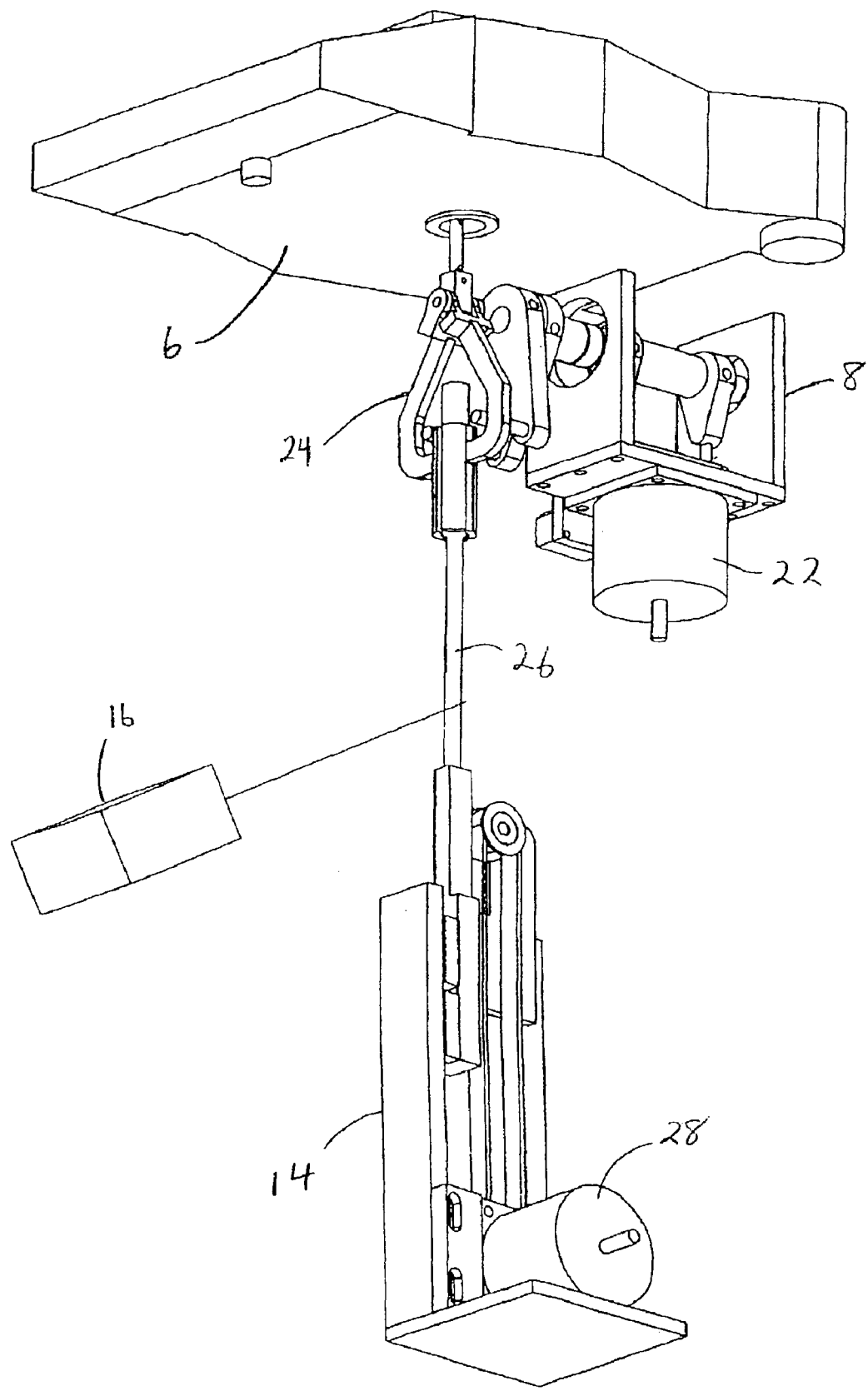
FIG. 4 is a perspective view of the balance, sample handling, sample lift, and rack detection/identification components of an embodiment of the apparatus (viewed as from lower right to upper left of the view of FIG. 1—sample racks, carrier, and frame not shown).

FIG. 4 shows the relative positioning and interaction between balance 6, sample handling assembly 8, and sample lift assembly 14. Gripper assembly 24 is shown holding a sample for weighing in conjunction with sample lifting assembly 14, powered by lifting motor 28. Sample handling assembly 8 includes gripper spreader motor 22. Although sample racks and sample rack carrier 10 are not shown in FIG. 4, scanner 16 is shown for the purpose of illustrating the relative positioning of components.

Figure 5:
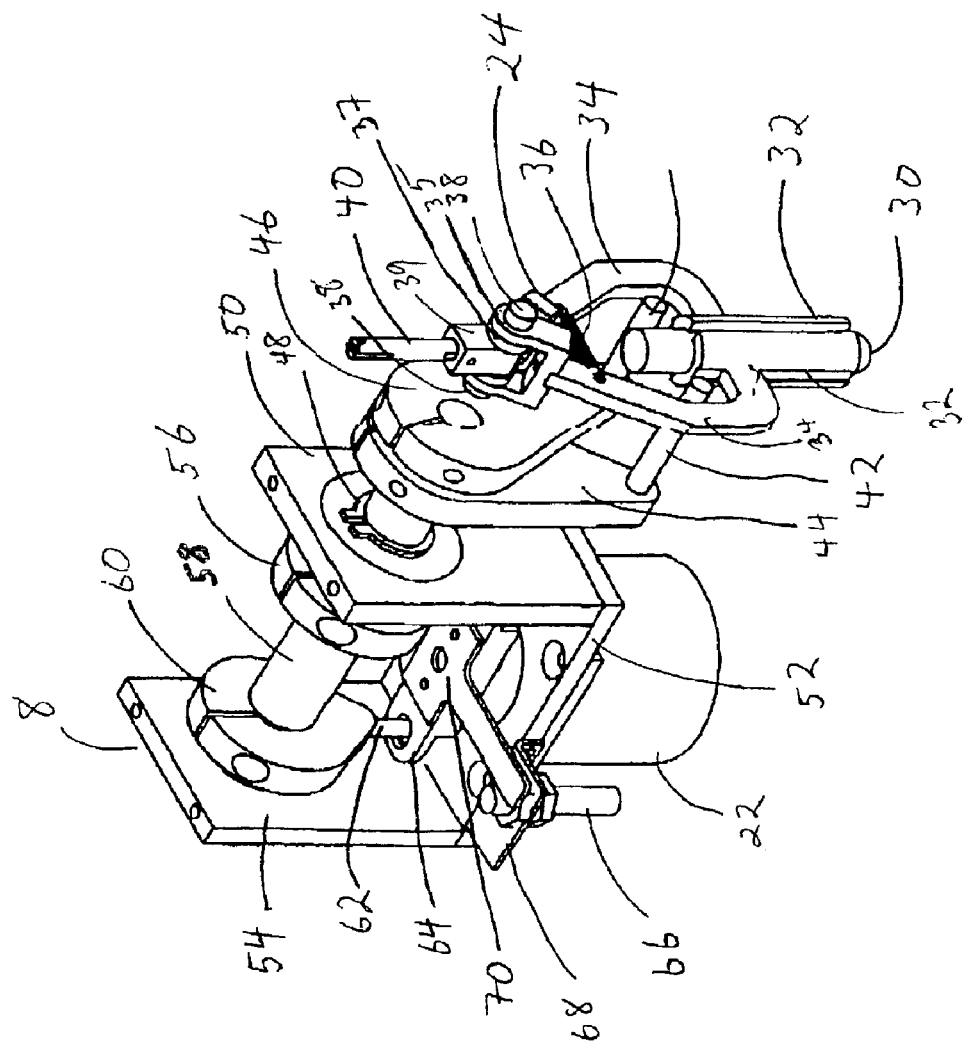
FIG. 5 is a top perspective view of an embodiment of the sample handling assembly.
Figure 6:
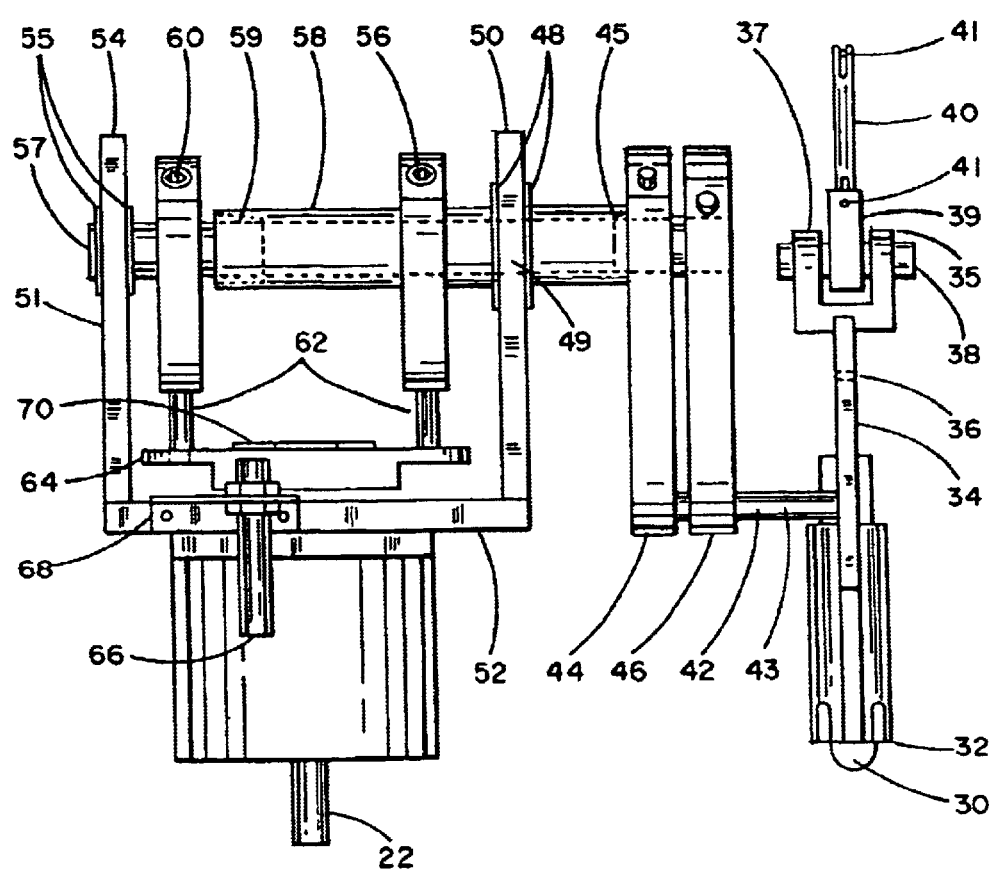
FIG. 6 is a side elevational view of an embodiment of the sample handling assembly.

FIG. 5 is an enlarged depiction of sample handling assembly 8. Gripper assembly 24 comprises gripper fingers 32 which directly contact sample container 30. Gripper fingers 32 are connected to gripper arms 34 which are urged toward one another by spring 36. Outer clevis 35 and inner clevis 37 connect the gripper arms 34 to mounting block 39 via shoulder screws 38. Mounting block 39 is connected to balance shaft 40 via dowel pin 41 (as shown in FIG. 6). Balance shaft 40 is connected to balance 6 (see FIG. 4) via dowel pin 41 (see FIG. 6).

Gripper arms 34 of gripper assembly 24 are spread (against the tension provided by spring 36) by dowels 42 and 43, which are connected to arm spreaders 44 and 46, respectively. Arm spreader 44 is connected to and actuated by outer shaft 58. Arm spreader 46 is connected to and actuated by inner shaft 57. Outer shaft 58 and inner shaft 57 are supported by bearing 49 as they pass through front mount 50. This connection is secured by snap rings 48, which are disposed forward and rearward of front mount 50. The rearward end of outer shaft 58 terminates prior to rear mount 54, and is supported in relation to inner shaft 57 by bronze bushing 59. Inner shaft 57 continues rearward through rear mount 54, where it is supported by bearing 51, and secured by snap rings 55.

Outer arm rotator 56 and inner arm rotator 60 are connected to outer shaft 58 and inner arm shaft 57, respectively. Arm rotators 56 and 60 are connected to rotator 64 via dowels 62. Rotator 64 is powered by stepper motor 22, to actuate arm rotators 56 and 60. The operation of rotator 64 is controlled by sensor 66 (e.g. an omron sensor), which operates via sensor flag 70. Sensor bracket 68 provides the platform for mounting of sensor 66 and sensor flag 70. The sensor assembly allow the coordination of the operation of sample handling assembly 8 with other components of the apparatus. In particular, operation of sample handling assembly 8 is coordinated with the operation of sample lift assembly 14.

FIGS. 7–10 show various detailed views of sample lift assembly 14. FIG. 7 is a front perspective view of the assembly; FIG. 8 is a front elevational view; FIG. 9 is a side elevational view (as from the right of FIG. 8); and FIG. 10 is a top elevational view of the assembly.

Lift motor 28, mounted in bracket 88 on platform 90, powers drive belt 78 via pulley 92. At the upper end of sample lift assembly 14, pulley 76 is mounted on an extension of rear mount 80 to carry drive belt 78. Side mount 81 is connected along one edge to rear mount 80, at its bottom to platform 90, and on the lower portion of its front side to bracket 88. On the side of drive belt 78 proximal to side mount 81, bracket 82 is connected to lift shaft mount 74. On the opposite side of lift shaft mount 74, brackets 84 provide a mounting platform for sensor components and travel stops, which are coordinated with sensor components and travel stops 86 mounted on side mount 81 to control range of operation and range of travel of lift shaft mount 74 in conjunction with the operation of lift motor 28 and the drive assembly. Lift shaft 26 is mounted in lift shaft mount 74 and terminated at the upper end with tip 72. Tip 72 may be configured variously, depending on the shape of the bottom of sample container 30. In a preferred embodiment, tip 72 is cup shaped at the top to allow handling of containers with round bottoms. Conical or flat bottom containers may be handled by configuring tip 72 accordingly, as will be recognized by the skilled artisan.

Figure 11:
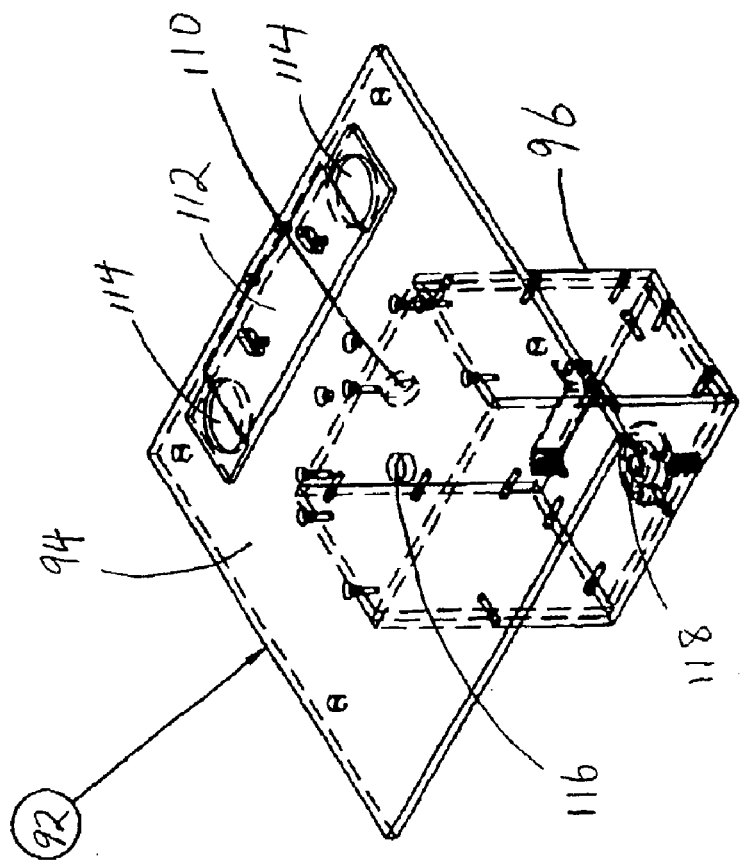
FIG. 11 is a top perspective view of an embodiment of the optional weighing isolation housing of the apparatus.
Figure 12:
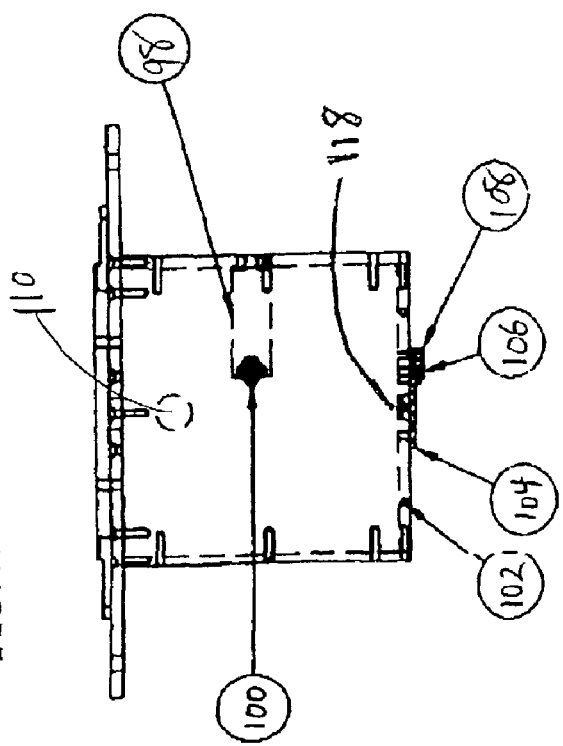
FIG. 12 is a side elevational view of an embodiment of the optional weighing isolation housing.

The forward portion of sample handling assembly 8 may be isolated to facilitate certain weighing operations which require greater isolation of the sample or control of the atmospheric environment during the operation. Housing 92 may be optionally installed to provide this capacity (see FIG. 13). FIGS. 11 and 12 provide a top perspective and front elevational view, respectively, showing details of housing 92 (apparatus not shown). Top mounting plate 94 is provided with connection apertures 114 and bracket 112 for connecting housing 92 to the bottom of balance 6. Aperture 116 allows passage of balance shaft 40 of the gripper assembly 24 to balance 6 when housing 92 is installed (gripper assembly 24 is contained within housing 92). The lower compartment 96 of housing 92 is a substantially rectangular box having front and rear, left and right, and bottom plate 102 (see FIG. 12), with the top formed by attachment of lower compartment 96 to top mounting plate 94. Aperture 110, in the rear side of lower compartment 96, allows passage of outer and inner shafts 58 and 57, such that gripper assembly 24 may be actuated within housing 92. FIG. 12 shows lifted sample sensor 100, secured by sensor bracket 98. Seated sample sensor 106 is secured by sensor bracket 108. Seated sample sensor 106 and bracket 108 are positioned adjacent to aperture 118, which allows lifting of a sample container 30 (see FIGS. 5 and 6) through bottom plate 102 by lifting assembly 14. Together this sensor arrangement allows precise coordination of the operation of lift assembly 14 and sample handling assembly 8, when housing 96 is utilized.

Figure 13:
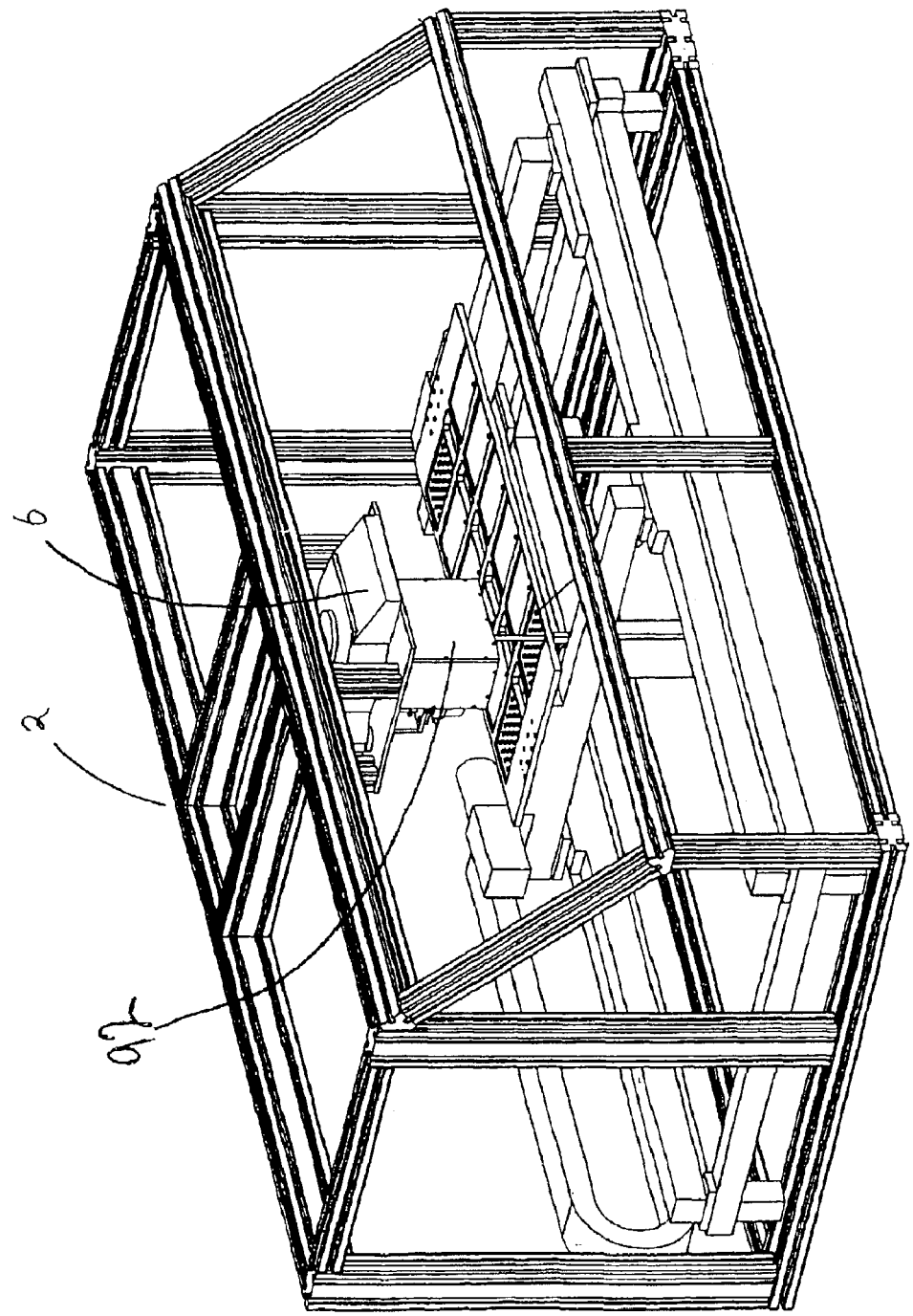
FIG. 13 is a front perspective view of one embodiment of the apparatus having the optional weighing isolation housing installed.

FIG. 13 shows an embodiment of automated weighing station 2, with housing 92 installed.

Figure 14:
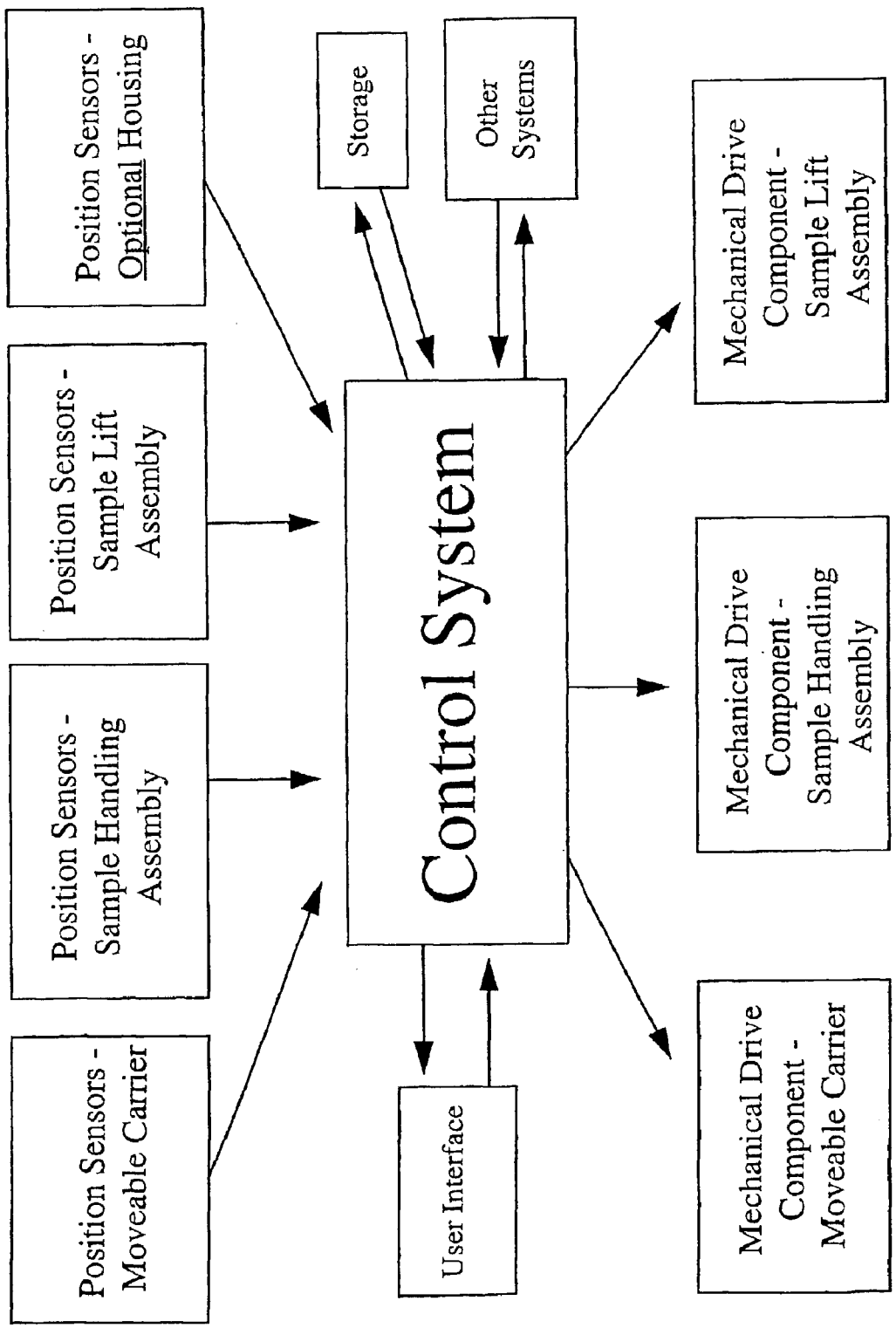
FIG. 14 is a block diagram of the control system, associated devices, and systems, according to one embodiment of the invention.

FIG. 14 provides a schematic overview of the various input and outputs of an embodiment of a data acquisition and control system for an automated apparatus of the present invention.

Figure 15:
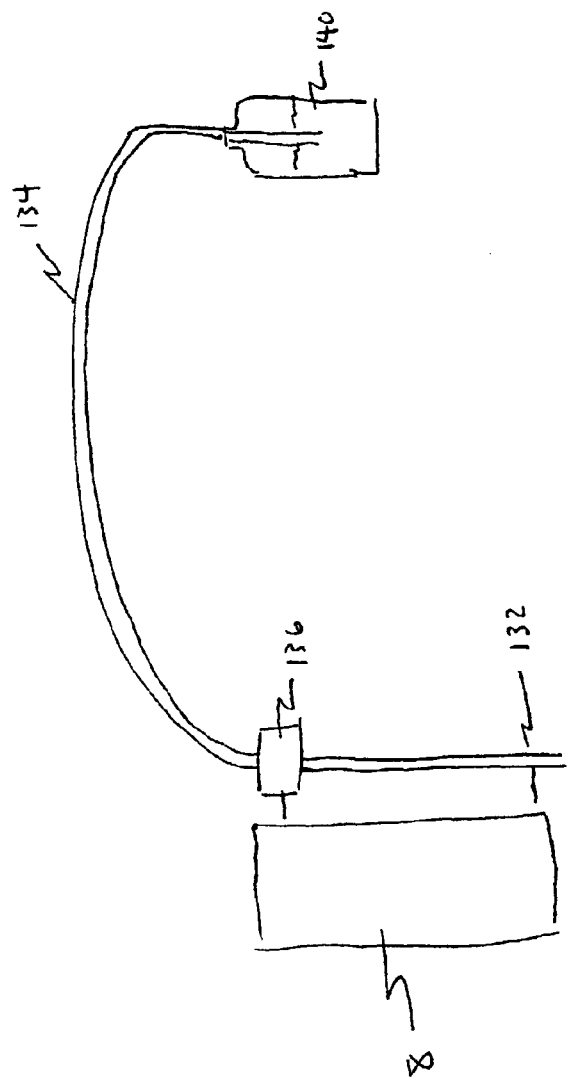
FIG. 15 illustrates a possible embodiment of a liquid dispensing apparatus of the present invention.

FIG. 15 provides a schematic diagram of a liquid dipenser for use in an automated system of the present invention. As shown in FIG. 15, a liquid dispenser may include dispensing means 132, disposed vertically above a sample container. Dispensing means 132 are connected via tubing 134 to a source of liquid 140. A pump or valve 136 may be utilized to control the flow of liquid through the liquid dispensing means. The liquid dispenser may be mounted to sample handling assembly 8 and move with the sample handling assembly in the manners described above with reference to the weighing apparatus.

In an embodiment of the present invention, the weighing or liquid dispensing apparatus may further comprise a positioning sensor system to sense the relative position of the sample lifting pin and/or sample gripper and prevent movement of the carrier apparatus unless the lifting pin is positioned so that it will not interfere with the movement. The positioning sensor system may comprise a laser, or a scanning laser, in combination with a receiver. The sensor system may further comprise one or more mirrors for directing the laser.

The sensor system may rely on an unbroken or unbroken laser beam to determine the relative position of component parts in the weighing or liquid dispensing system. For example, in an embodiment of the present invention, a sensor system may comprise a laser beam generator that emits a laser beam that is sensed by a receiver located in a second position. The laser beam generator and receiver may be positioned on the frame of the apparatus at a height such that weighing of a sample will cause the beam to be broken. A data acquisition and control system may communicate with the receiver such that a break in the beam will instruct the control system to restrict movement of one or more component parts of the weighing or liquid dispensing apparatus.

In an embodiment, the system checks to see if the sample is back in its position with the proper clearance for movement of the table. A scanning laser that covers the area under the gripper and the hole where the sample travels to the gripper insures this.

The system may in addition, or in the alternative, check to see if the lifting pin is back in its position with the proper clearance for movement of the table. The scanning laser that covers the area under the gripper and the hole where the pin lefts the sample to the gripper insures this. Another sensor on the lifting pin assembly insures that the pin is in the home position.

The sensor system may also check to see if the sample is properly placed in the gripper before the weighing process starts. A sensor may be utilized within the gripper assembly to insure that the sample is in the proper position and it is hanging freely in the gripper without any contact with other objects.

In a further embodiment, a weighing and/or liquid dispensing apparatus of the present invention may further comprise a bar code scanner. The bar code scanner may be mounted on the rack support assembly and positioned to read bar codes that have been applied to racks of test tubes. The bar code scanner may be linked electronically to a data acquisition and control system and feed data into the system. Suitable bar code scanning equipment is commercially available from a variety of sources, including IBM, Symbol, Cognex and NCR.

Figure 16:
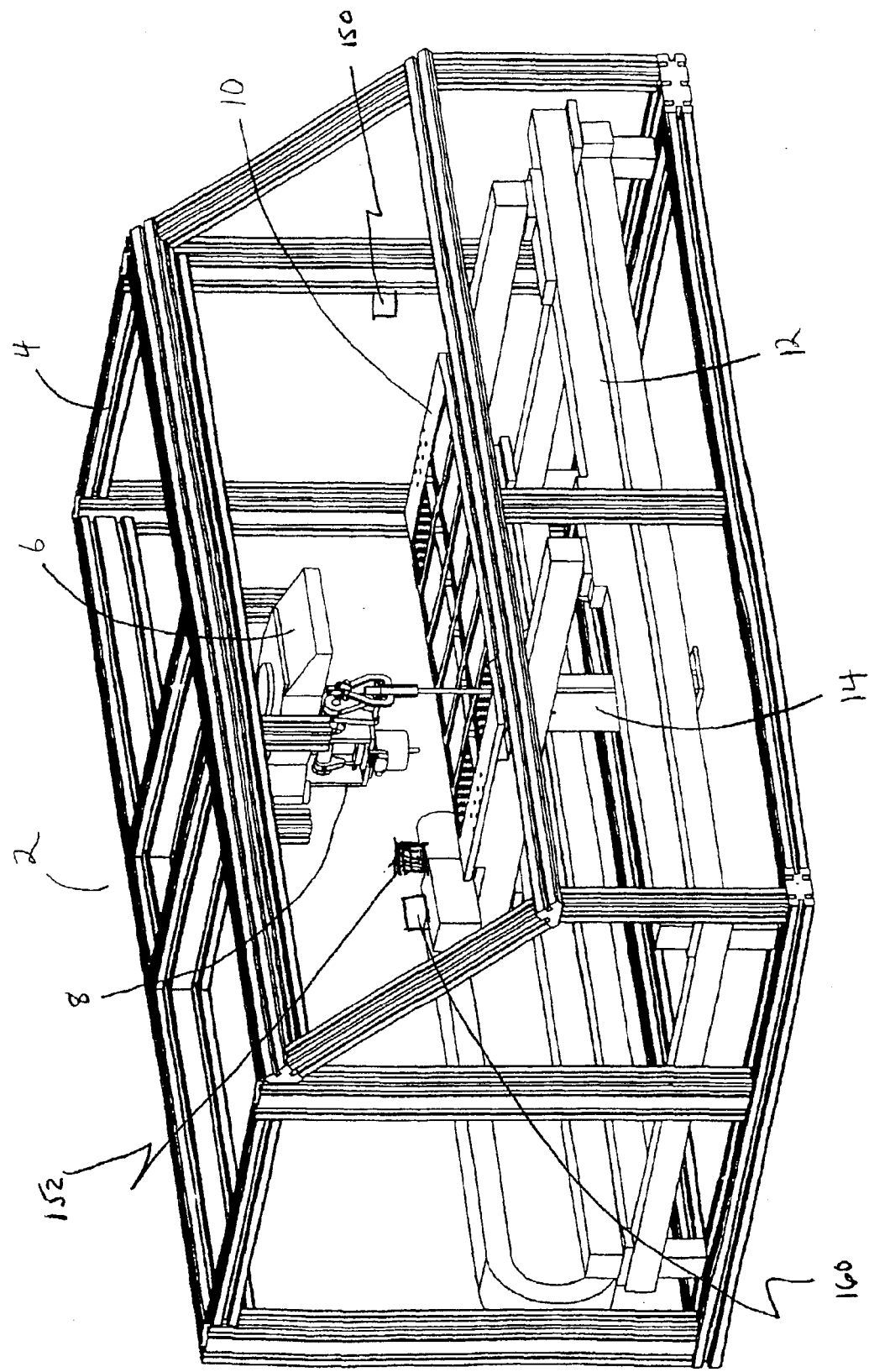
FIG. 16 is a front perspective view of an embodiment of an apparatus of the present invention showing a laser sensing system.

FIG. 16 illustrates as embodiment of the present invention comprising a laser sensing system. As shown in FIG. 16, a laser generator 150 may be mounted on the apparatus and positioned to send a laser beam to receiver 152. The path of the laser comprises a plane just above the level of sample containers in the racks. The laser beam is broken when sample containers are lifted or picked up to be weighed. If a sample container is not returned correctly to its position in the rack, the laser beam will remain broken. Receiver 152 communicates with a data acquisition and control system and halts operation of the apparatus while the beam remains broken.

FIG. 16 also illustrates a possible positioning of a bar code scanning unit 160. The bar code scanning unit is positioned to be able to read bar codes contained on sample container racks. Information from the bar code scanner is fed into a data acquisition and control system to assist in controlling and monitoring aspects of the apparatus.

As described above, an aspect of the present invention is a data acquisition and control system. FIG. 14, referred to above, provides an overview of the types of information and data that may be handled by the system. FIGS. 17–20 provide screenshots from the display of an embodiment of a data acquisition and control system of the present invention.

As shown if FIG. 17, the system may be configured to provide different types of data relating to each rack of sample containers in the system. The racks may be tracked through the weighing and/or liquid dispensing system and data stored relating to the time of weighing etc.

Figure 18:
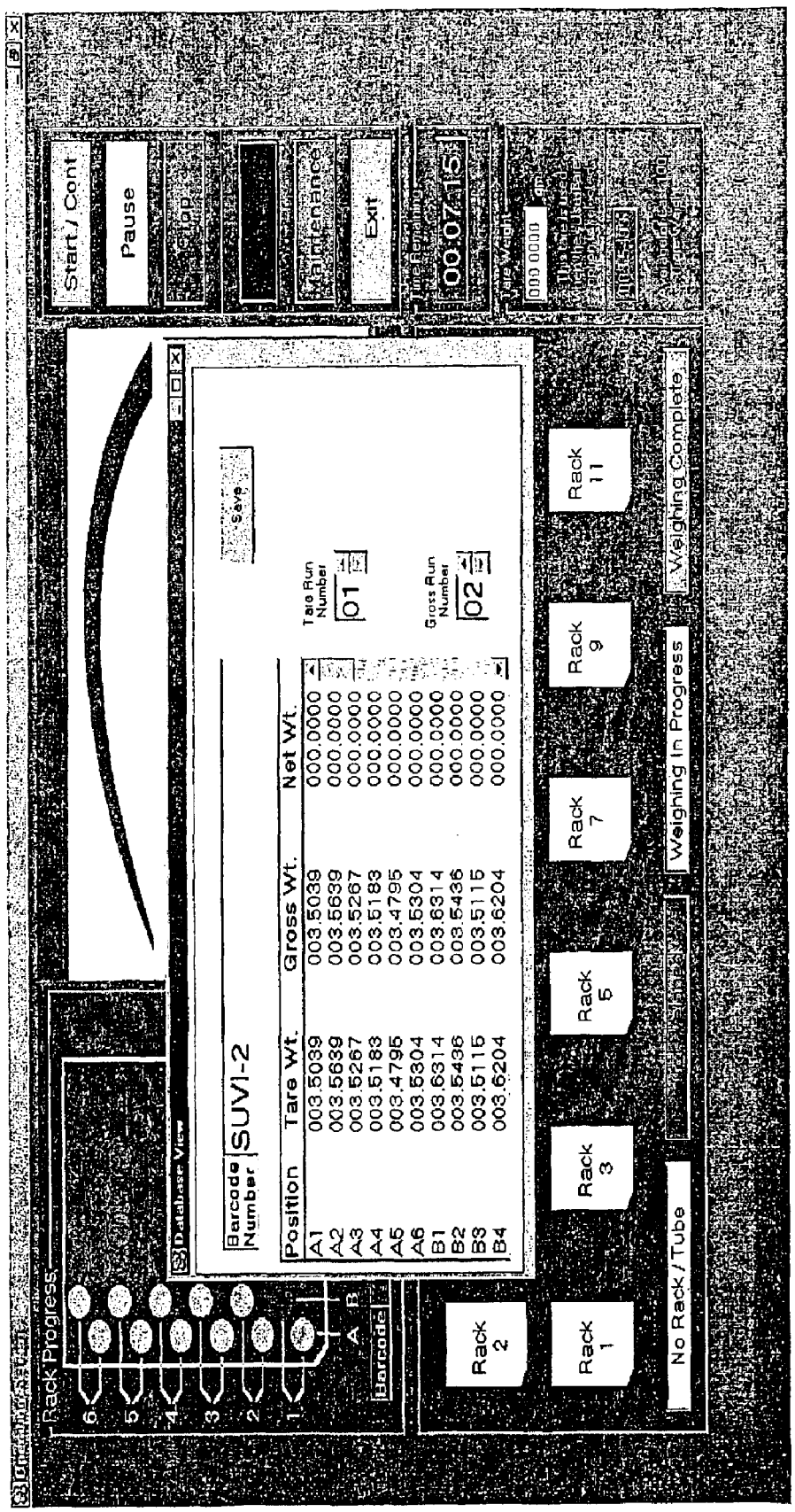
Figure 19:
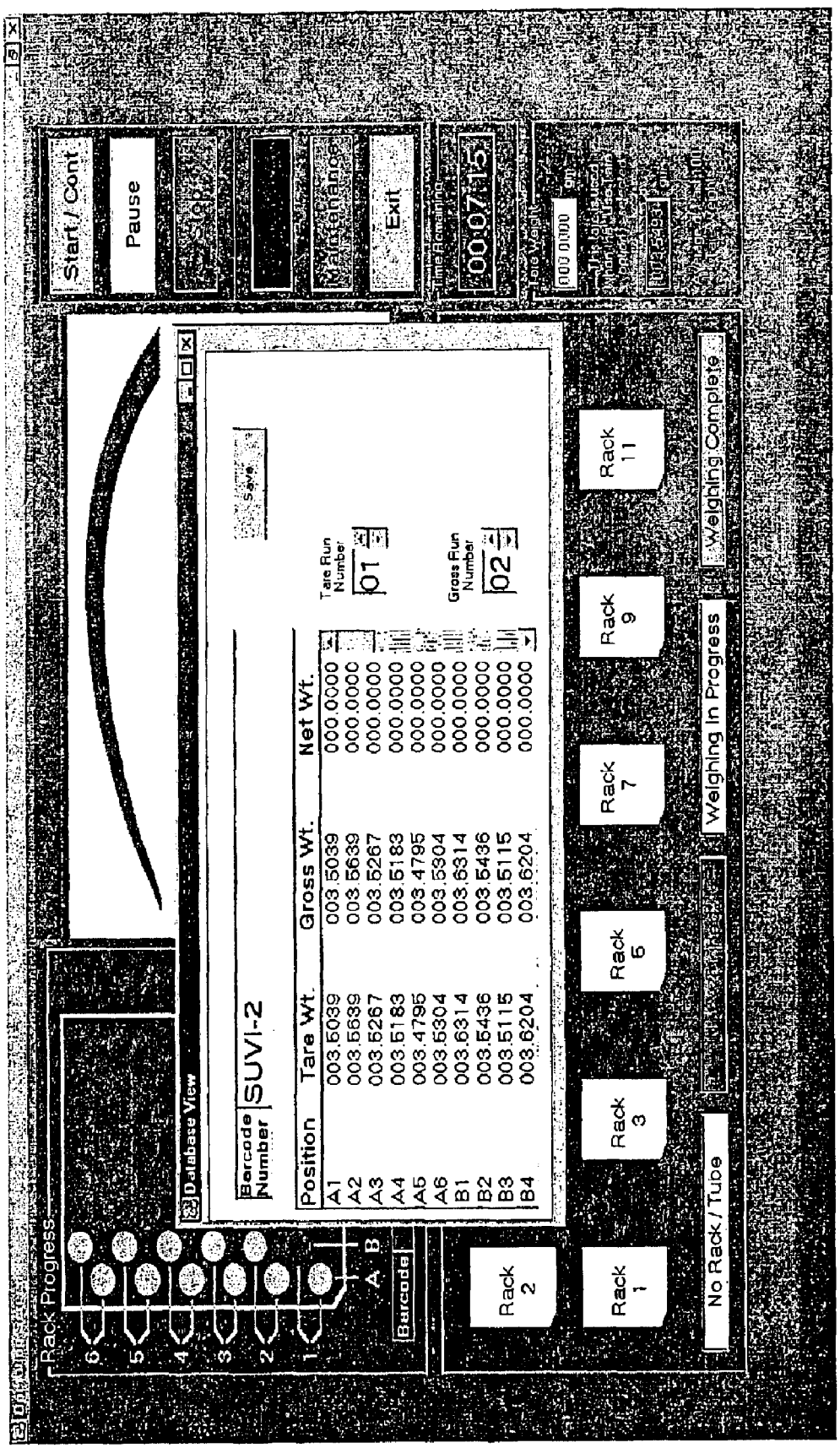

FIGS. 18 and 19 illustrates a graphical display providing information relating to a single rack and the sample containers in the rack. The system software may be fully integrated and interfaced to different types of databases like ORACLE or ACCESS. All data may be stored in many formats including but not limited to ODBC so it can be loaded directly in the database and in ASCII reports for further manipulations. These reports are complete and error-free with details about sample I.D., rack number, position, tare weight, gross weight, net weight and/or volume of liquid delivered for each sample.

Figure 20:
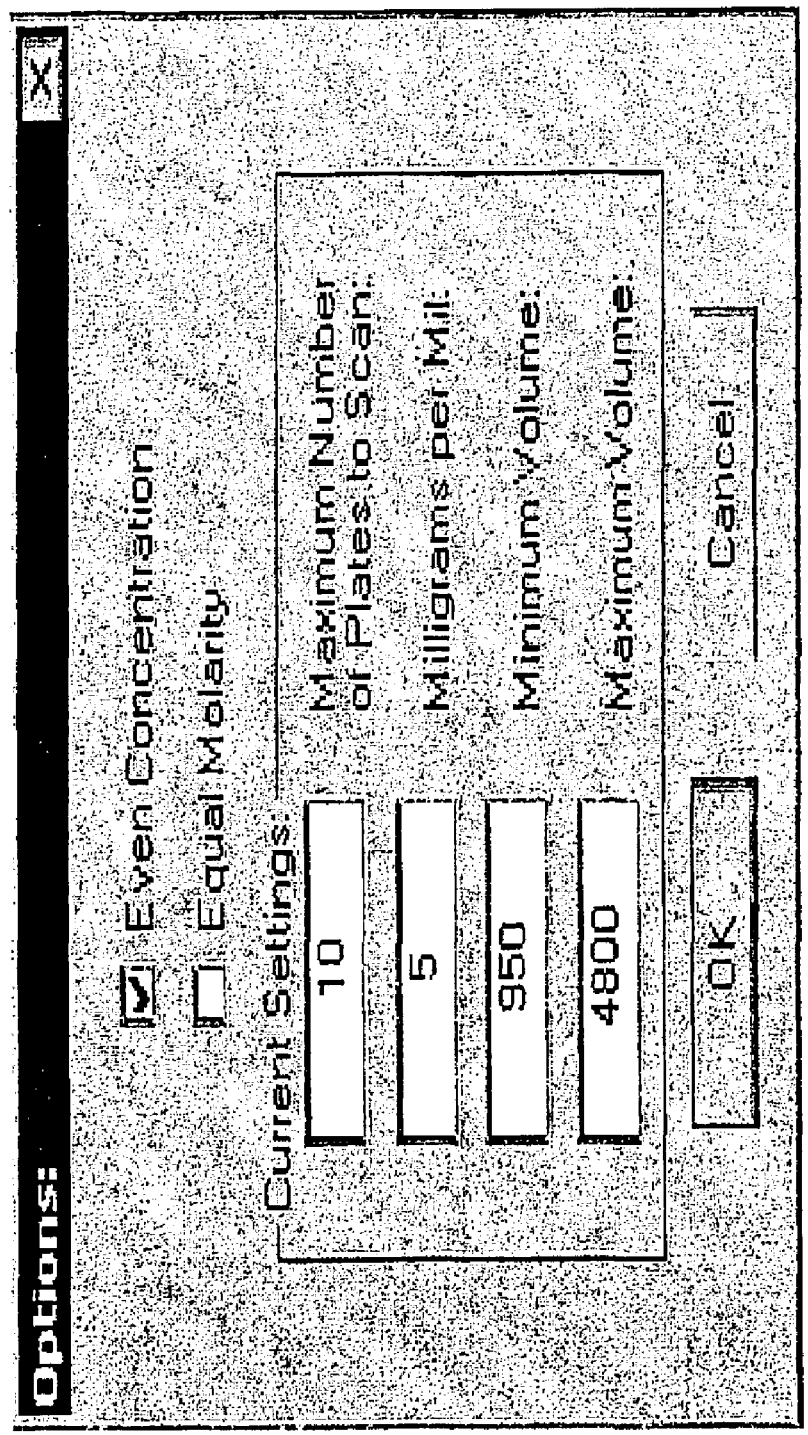

FIG. 20 illustrates a graphical display providing options for liquid dispensing. As shown in FIG. 20 liquid delivery of many solvents than can be delivered to fresh tubes or vials or to samples for dilution, and different concentrations in multiple formats.

It will thus be seen that the objects set forth, among those made apparent from the preceding description, are efficiently obtained and, since certain changes may be made in carrying out the above embodiments and in the apparatus and method set forth, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. An automated weighing station comprising:
  a) a support frame;
  b) a balance secured to said support frame;
  c) a sample handling assembly operably connected to said balance and secured to said balance;
  d) a moveable carrier capable of moving samples in at least a plurality of directions for moving samples into position beneath said sample handling assembly;
  e) a lift assembly positioned beneath said moveable carrier and said sample handling assembly for lifting samples into position to be accessed by said sample handling assembly;
  f) a control system for controlling said sample handling assembly, said lift assembly, and said moveable carrier in a coordinated manner, and for storing weight measurements of individual samples; and
  g) a liquid dispensing system, the liquid dispensing system comprising a liquid dispenser operably connected to the sample handling assembly.

2. An automated weighing station of claim 1, wherein said sample handling assembly further comprises:
  a) a gripper assembly comprising arms, one end of each arm being pivotably connected along a common pivot axis, and the opposite end of each arm comprising a gripper finger adapted to directly contact a sample container, and a spring tensioner urging said arms toward one another; and
  b) a powered mechanical drive component in communication with said gripper assembly.

3. An automated weighing station of claim 2, wherein said mechanical drive component operates intermittently to spread said gripper arms against the force of said spring tensioner, thereby increasing the distance between said gripper fingers of the respective gripper arms such that a sample may be received therein, to be gripped by said fingers when said mechanical drive component releases said arms to return to a closed position as urged by said spring tensioner.

4. An automated weighing station of claim 1, further comprising a housing adapted to isolate a gripper assembly of said sample handling assembly.

5. An automated weighing station of claim 4, wherein said housing comprises a first sensor associated with an aperture for receiving a sample through a bottom plate of said housing, and a second sensor positioned adjacent to said gripper assembly, said first and second sensors allowing determination of a lowered position and a lifted position, respectively, of said sample.

6. The system of claim 1 wherein the liquid dispensing system and the weighing system are synchronized.

7. The system of claim 6 wherein the synchronization results in the liquid dispensing and the weighing of the samples occurring in substantially the same amount of time as would have been taken to weigh the samples.

8. An automated weighing station of claim 1, wherein said moveable carrier comprises:
   a) a sample rack carrier; and
   b) a carrier support unit.

9. An automated weighing station of claim 8, further comprising position sensors adapted to communicate the position of said sample rack carrier in relation to said gripper assembly, to said control system such that weight measurements of individual samples are stored electronically, and are associated with an individual sample by at least one identifying characteristic.

10. An automated weighing station of claim 8, wherein said sample racks are characterized by an asymmetric shape which requires that said sample racks be placed in said sample rack carrier in only one possible orientation relative to said moveable carrier.

11. An automated weighing station of claim 8, wherein said sample rack carrier is adapted to hold at least one rack which is adapted to hold a plurality of sample containers.

12. An automated weighing station of claim 8, wherein said sample rack carrier is adapted to allow access by said lift assemble to at least one sample container from beneath said sample rack carrier.

13. An automated weighing station of claim 8, wherein said carrier support unit further comprises at least one powered mechanical drive component adapted to provide controlled forward and rearward, left and right movement of said sample rack carrier.

14. An automated weighing station of claim 13, where said at least one powered mechanical drive component comprises a first electric motor controlling forward and rearward movement, and a second electric motor controlling left and right movement of said sample rack carrier.

15. An automated weighing station of claim 8, further comprising a scanner for determining the identity of sample racks within an array of racks held by said sample rack carrier.

16. An automated weighing station of claim 15, wherein said sample rack carrier comprises openings such that said scanner may determine the identity of sample racks disposed within the interior of said array of racks.

17. An automated weighing station of claim 15, wherein said sample racks are identified by said scanner utilizing a bar coding system.

18. An automated weighing station of claim 1, wherein said lift assembly comprises:
   a) a housing;
   b) a powered mechanical drive component connected to said housing; and
   c) a lift shaft operably connected to said powered mechanical drive component,
      wherein said powered mechanical drive component provides controlled upward and downward movement of said lift shaft.

19. An automated weighing station of claim 18, wherein said lift shaft further comprises a tip which is adapted to receive the bottom portion of a sample container.

20. An automated weighing station of claim 19, wherein said tip is adapted to receive a bottom portion of a sample container, the shape of which is selected from the group consisting of rounded, conical, flat-ended cubical, and flat-ended circular.

21. An automated weighing station of claim 18, wherein said powered mechanical drive component comprises an electric motor having a pulley engaged to a belt member, the distal portion of which engages a second pulley, and wherein said belt member is attached to a lift shaft mount to provide upward and downward motion of said lift shaft which is connected to said lift shaft mount.

22. An automated weighing station of claim 21, wherein said housing further comprises at least one aperture for the introduction of gases for atmospheric control within said housing.

23. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, dispensing a liquid into a sample container, weighing the sample container, storing the weight and position of the sample, and returning said at least one sample container to said ordered array after a weight measurement is taken, wherein said gripper assembly is connected to a balance and is disengaged from other components of said sample handling assembly while said weight measurement is taken.

24. A method of claim 23, wherein the weight of a sample within the individual sample container is between about 0.01 mg and about 500 g.

25. A method of claim 23, wherein the weight of a sample within the individual sample container is between about 0.1 mg and about 50 g.

26. A method of claim 23, wherein the weight of a sample within the individual sample container is between about 1 mg and about 5 g.

27. A method of claim 23, wherein the weight of a sample within said individual sample container is between about 1 mg and about 100 mg.

28. A method of claim 23, wherein the weight of a sample within said individual sample container is between about 2 mg and about 50 mg.

29. A method of claim 23, wherein the weight of a sample within said individual sample container is between about 5 mg and about 25 mg.

30. A weighing system for automated weighing of samples, said system comprising:
   a) a support frame;
   b) a balance secured to said support frame;
   c) a sample handling assembly operatively connected to said balance and secured to said balance;

d) a moveable carrier capable of moving samples in at least a plurality of directions for moving samples into position beneath said sample handling assembly;

e) a lift assembly positioned beneath said moveable carrier and said sample handling assembly for lifting samples into position to be accessed by said sample handling assembly;

f) a data handling system for storing and processing of weight measurements of said samples; and g) a liquid dispensing system, the liquid dispensing system comprising a liquid dispenser operably connected to the sample handling assembly.

31. A weighing system of claim 30, wherein said data handling system comprises a balance; computer software; and computer hardware; wherein said data handling system is adapted to communicate weight measurements to computer software and hardware.

32. A weighting system of claim 31, wherein said data handling system further comprises one or more data collectors positioned and adapted to transmit information to a computer control unit, thereby allowing coordinated movement of samples via said sample handing assembly, said moveable carrier, and said lift assembly, wherein said information is coordinated by said computer control unit with the storage of weight measurement transmitted by said balance for individual samples.

33. A weighing system of claim 31, wherein said data handling system further comprises a scanner for detection of the position and identity of sample racks on said moveable carrier; at least one position sensor associated with said moveable carrier; and at least one sample position sensor associated with said sample handling assembly.

34. A weighing system of claim 31, wherein said computer hardware comprises one or more of the following: a display; data entry apparatus; a processor; an interface to the weighing apparatus; a printer or other output apparatus; electronic interfaces among the component parts; and memory.

35. A weighing system of claim 31, wherein said computer software comprises an operating system; a database program; a report generating program; a data-receiving program for receiving data from the weighing apparatus; and a control program for controlling the weighing apparatus.

36. A weighing system of claim 35, wherein said report generating program is adapted to provide data comprising individual sample identification related one or more of sample rack identity, sample position, tare weight of a sample container, gross weight of sample and sample container, and net weight of said sample.

37. A weighing system of claim 36, wherein said data is originally stored in a format selected from the group consisting of ASCII text, binary, and ODBC (object database connectivity format).

38. A weighing system of claim 36, wherein said data is originally stored in ASCII text format.

39. A liquid dispensing system for automated dispensing of liquid into sample containers, said system comprising:

a) a support frame;

b) a liquid dispenser secured to said support frame;

c) a sample container handling assembly operatively connected to said liquid dispenser;

d) a moveable carrier for moving sample containers into position beneath said liquid dispenser; and e) a data handling system for storing and processing of liquid delivery to said sample containers, wherein said data handling system comprises computer software and computer hardware, wherein said computer software comprises an operating system; a database program; a report generating program; a data-receiving program for receiving data from the liquid dispensing apparatus; and a control program for controlling the liquid dispensing apparatus, wherein said data handling system is adapted to communicate liquid dispensing measurements to computer software and hardware.

40. The system of claim 39, wherein said data handling system further comprises one or more data collectors positioned and adapted to transmit information to a computer control unit, thereby allowing coordinated movement of sample containers via said sample container handing assembly and said moveable carrier, wherein said movement information is coordinated by said computer control unit with the dispensing of liquid for individual sample containers.

41. The system of claim 40, wherein said data handling system further comprises a scanner for detection of the position and identity of sample container racks on said moveable carrier; at least one position sensor associated with said moveable carrier; and at least one sample position sensor associated with said sample container handling assembly.

42. The system of claim 40, wherein said computer hardware comprises one or more of the following: a display; data entry apparatus; a processor; an interface to the liquid dispensing apparatus; a printer or other output apparatus; electronic interfaces among the component parts; and memory.

* * * * *